(12) United States Patent
Kim et al.

(10) Patent No.: US 8,214,027 B2
(45) Date of Patent: *Jul. 3, 2012

(54) CARDIAC RHYTHM TEMPLATE GENERATION SYSTEM AND METHOD

(75) Inventors: Jaeho Kim, Redmond, WA (US); William Hsu, Ann Arbor, MI (US); Joseph Bocek, Seattle, WA (US); Harley White, Carnation, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 868 days.

This patent is subject to a terminal disclaimer.

(21) Appl. No.: 12/080,891

(22) Filed: Apr. 7, 2008

(65) Prior Publication Data

US 2008/0234770 A1    Sep. 25, 2008

Related U.S. Application Data

(63) Continuation of application No. 10/802,001, filed on Mar. 16, 2004, now Pat. No. 7,354,404, which is a continuation of application No. 09/845,987, filed on Apr. 30, 2001, now Pat. No. 6,708,058.

(51) Int. Cl.
*A61B 5/0464* (2006.01)
(52) U.S. Cl. .................................................. 600/515
(58) Field of Classification Search .......... 600/508–510, 600/515, 516, 519–521; 607/25
See application file for complete search history.

(56) References Cited

U.S. PATENT DOCUMENTS

| | | | |
|---|---|---|---|
| 4,336,810 A | 6/1982 | Anderson et al. | |
| 4,589,420 A | 5/1986 | Adams et al. | |
| 5,000,189 A | 3/1991 | Throne et al. | |
| 5,113,869 A | 5/1992 | Nappholz et al. | |
| 5,215,098 A * | 6/1993 | Steinhaus et al. | 600/515 |
| 5,215,099 A | 6/1993 | Haberl et al. | |
| 5,217,021 A | 6/1993 | Steinhaus et al. | |
| 5,447,519 A * | 9/1995 | Peterson | 607/5 |
| 5,779,645 A | 7/1998 | Olson et al. | |
| 5,817,027 A | 10/1998 | Arand et al. | |
| 5,857,977 A | 1/1999 | Caswell et al. | |
| 6,035,232 A | 3/2000 | Thong et al. | |
| 6,052,620 A | 4/2000 | Gillberg et al. | |
| 6,067,471 A | 5/2000 | Warren | |
| 6,076,014 A | 6/2000 | Alt | |
| 6,312,388 B1 | 11/2001 | Marcovecchio et al. | |
| 6,449,503 B1 * | 9/2002 | Hsu | 600/518 |
| 6,526,313 B2 | 2/2003 | Sweeney et al. | |
| 6,708,058 B2 * | 3/2004 | Kim et al. | 600/510 |

(Continued)

OTHER PUBLICATIONS

Notice of Allowance dated Aug. 16, 2007 from U.S. Appl. No. 10/802,001, 7 pages.

(Continued)

*Primary Examiner* — George Evanisko

(74) *Attorney, Agent, or Firm* — Hollingsworth & Funk, LLC

(57) ABSTRACT

A method and system provides for generating a snapshot representative of one beat of a patient's normal cardiac rhythm. Cardiac rate channel signals and shock channel signals are sensed. A fiducial point is determined for a predefined number of the cardiac rate channel signals. A predefined number of the shock channel signals are aligned using the fiducial point. A template is generated using the aligned shock channel signals, whereby the template is representative of one of the patient's normal supra-ventricular conducted cardiac beats. The template is updated on a periodic basis.

22 Claims, 13 Drawing Sheets

U.S. PATENT DOCUMENTS

| | | | |
|---|---|---|---|
| 6,745,068 B2 * | 6/2004 | Koyrakh et al. | 600/515 |
| 7,062,315 B2 | 6/2006 | Koyrakh et al. | |
| 7,184,818 B2 | 2/2007 | Kim | |
| 7,354,404 B2 * | 4/2008 | Kim et al. | 600/508 |
| 7,529,581 B2 | 5/2009 | Kim | |
| 2002/0193695 A1 | 12/2002 | Koyrakh et al. | |
| 2009/0222054 A1 | 9/2009 | Kim | |

OTHER PUBLICATIONS

Office Action Response dated Apr. 12, 2007 from U.S. Appl. No. 10/802,001, 9 pages.
Office Action dated Dec. 5, 2006 from U.S. Appl. No. 10/802,001, 6 pages.
Notice of Allowance dated Oct. 30, 2006 from U.S. Appl. No. 10/105,875, 6 pages.
Office Action Response dated Aug. 11, 2006 from U.S. Appl. No. 10/105,875, 17 pages.
Office Action dated May 6, 2006 from U.S. Appl. No. 10/105,875, 10 pages.
Office Action Response dated Mar. 6, 2006 from U.S. Appl. No. 10/105,875, 18 pages.
Office Action dated Feb. 14, 2006 from U.S. Appl. No. 10/105,875, 3 pages.
Office Action Response dated Feb. 3, 2006 from U.S. Appl. No. 10/105,875, 19 pages.
Office Action dated Nov. 1, 2005 from U.S. Appl. No. 10/105,875, 13 pages.
Office Action Response dated Aug. 8, 2005 from U.S. Appl. No. 10/105,875, 23 pages.
Office Action dated May 4, 2005 from U.S. Appl. No. 10/105,875, 6 pages.
Office Action Response dated Jan. 19, 2005 from U.S. Appl. No. 10/105,875, 3 pages.
Office Action dated Dec. 8, 2004 from U.S. Appl. No. 10/105,875, 4 pages.
Notice of Allowance dated Dec. 31, 2008 from U.S. Appl. No. 11/711,329, 7 pages.
Office Action Response dated Oct. 29, 2008 from U.S. Appl. No. 11/711,329, 9 pages.
Office Action dated Sep. 19, 2008 from U.S. Appl. No. 11/711,329, 5 pages.
File History for U.S. Appl. No. 12/435,904.
Medtronic, GEM III VR 7231—Implantable Cardioverter Defibrillator System Reference Guide, Feb. 2001, 354 pages.

* cited by examiner

CARDIAC RHYTHM TEMPLATE GENERATION SYSTEM AND METHOD

RELATED PATENT DOCUMENTS

This application is a continuation of U.S. patent application Ser. No. 10/802,001 filed on Mar. 16, 2004, now U.S. Pat. No. 7,354,404, which is a continuation of U.S. patent application Ser. No. 09/845,987 filed on Apr. 30, 2001, now U.S. Pat. No. 6,708,058, both of which are incorporated herein by reference.

FIELD OF THE INVENTION

The present invention relates generally to implantable medical devices and, more particularly, to generating, with an implantable medical device, a template representative of one beat of a patient's normal cardiac rhythm.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiologic disturbances caused by a disease process or from an electrical disturbance, the heart is denoted to be arrhythmic. The resulting cardiac arrhythmia impairs cardiac efficiency and can be a potential life threatening event.

Cardiac arrhythmias occurring in the atria of the heart, for example, are called supra-ventricular tachyarrhythmias (SVTs). SVTs take many forms, including atrial fibrillation and atrial flutter. Both conditions are characterized by rapid, uncoordinated contractions of the atria. Besides being hemodynamically inefficient, the rapid contractions of the atria can also adversely effect the ventricular rate. This occurs when the aberrant contractile impulse in the atria are transmitted to the ventricles. It is then possible for the aberrant atrial signals to induce ventricular tachyarrhythmias.

Cardiac arrhythmias occurring in the ventricular region of the heart, by way of further example, are called ventricular tachyarrhythmias. Ventricular tachycardia (VTs), for example, are conditions denoted by a rapid heart beat, 150 to 250 beats per minute, that has its origin in some abnormal location with the ventricular myocardium. The abnormal location typically results from damage to the ventricular myocardium from a myocardial infarction. Ventricular tachycardia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious ventricular tachyarrhythmias. ICDs are able to recognize and treat tachyarrhythmias with a variety of tiered therapies. These tiered therapies range from providing anti-tachycardia pacing or cardioversion energy for treating ventricular tachycardia to defibrillation energy for treating ventricular fibrillation. To effectively deliver these treatments, the ICD must first identify the type of tachyarrhythmia that is occurring, after which appropriate therapy is provided to the heart. In order to apply the proper therapy in responding to an episode of tachyarrhythmia, the ICD may compare sensed cardiac signals to a previously stored normal sinus rhythm (NSR) signal waveform. It is appreciated that the stored NSR signal waveform must accurately characterize a patient's true normal sinus rhythm in order to properly identify potentially fatal deviations from normal cardiac activity.

For the reasons stated above, and for other reasons stated below which will become apparent to those skilled in the art upon reading the present specification, there is a need in the art for reliably and accurately characterizing a patient's normal cardiac rhythm. There exists a further need for such an approach that is adaptive and accommodates changes in the patient's normal cardiac rhythm over time. The present invention fulfills these and other needs.

SUMMARY OF THE INVENTION

The present invention is directed to a method and system for generating a snapshot representative of one beat of a patient's normal cardiac rhythm. In accordance with one embodiment of the present invention, rate channel signals and shock channel signals are sensed. A fiducial point for the rate channel signals is determined. The shock channel signals are aligned using the fiducial point. A template is generated using the aligned shock channel signals. The template is representative of one of the patient's normal supra-ventricular conducted beats. The template may be updated on a periodic basis, such as several times per day.

Using subsequently detected beats, confirmation processes are carried out prospectively to confirm that the generated template is representative of one of the patient's normal supra-ventricular conducted beats. According to one approach, a confirmation process uses subsequently detected template beats to determine whether the generated template is or is not representative of one of the patient's normal supra-ventricular conducted beats.

One confirmation process involves determining that no template is presently stored, and, in response to confirming that each of a number of subsequently detected template beats correlates with the generated template, storing the generated template. Another confirmation process involves determining that no template is presently stored, and discarding the generated template in response to confirming that each of a number of subsequently detected template beats fails to correlate with the generated template. A further confirmation process involves determining that a template is presently stored, and retaining the stored template in response to determining that each of a number of subsequently detected template beats correlates with the stored template.

Another confirmation process involves determining that a template is presently stored, generating a new template in response to confirming that each of a number of subsequently detected template beats fails to correlate with the stored template, and replacing the stored template with the new template in response to confirming that each of a number of newly detected template beats correlates with the new template. A further confirmation process involves determining that a template is presently stored, generating a new template in response to the confirming that each of a number of subsequently detected template beats fails to correlate with the stored template, and retaining the stored template and discarding the new template in response to confirming that each of a number of newly detected template beats fails to correlate with the new template.

The template generation methodology typically involves averaging or median filtering the aligned shock channel signals. For example, averaging the aligned shock channel signals involves point-by-point averaging or median filtering of n samples acquired from the same time location of aligned n template beats. The template generation methodology also involves determining that the rate channel signals satisfy predefined normalcy criteria using a running average (RRavg) of a number of RR intervals.

For example, after initiating template updating, a running average (RRavg) of a number of RR intervals is compared to a predetermined rate threshold. If RRavg is less than a predetermined interval, template updating is suspended. By way of further example, a beat is classified as a regular beat if an RR interval associated with the beat falls within a predetermined percentage range of RRavg. Further, a heart rate is classified as regular if a predetermined percentage of the beats are regular beats.

Template generation may also involve skipping processing of a subsequently sensed rate channel signal if the subsequently sensed rate channel signal is detected before processing of a current sensed rate channel signal is completed. The rate channel is also monitored for noise. If the rate channel is determined to be noisy, the beat measured from the noisy rate channel is classified as a noisy beat.

An automatic gain control (AGC) operation of the template generation methodology involves computing an average peak amplitude of a number of beats. The shock channel gain is adjusted to an available gain that sets the average peak amplitude to a predetermined percentage of a maximum ADC (analog-to-digital converter) value, such as 60% of the maximum ADC value.

According to further template generation operations, sensed beats are classified as NSR beats in response to satisfying a first set of criteria. NSR beats are classified as template beats in response to satisfying a second set of criteria. Generating the template, according to this embodiment, includes generating the template using the aligned template beats.

The fiducial point to which the shock channel template waveforms are time aligned is characterized by a fiducial point type. The fiducial point type is determined by determining the larger of a positive peak and a negative peak for each of a number of NSR beats. The fiducial point type for alignment is determined by determining whether the majority of NSR beats have positive peaks or negative peaks. Aligning the shock channel signals involves aligning shock channel waveforms of template beats centered with respect to the fiducial point. A template waveform is generated by averaging a predetermined number of the time aligned template beats.

Generating the template further involves determining a number of features of the template. The template features include an absolute maximum peak and at least one of a turning point and a flat slope point.

A body implantable system preferably implements a template generation methodology of the present invention. The body implantable system is disposed in a housing having a can electrode. A lead system extends from the housing into a heart and includes electrodes. A detector system, coupled to the lead system, detects rate channel signals and shock channel signals sensed by one or both of the lead system electrodes and the can electrode. A control system, which includes a controller and a tachyarrhythmia detector/template generator, is coupled to the detector system. The control system determines a fiducial point for the rate channel signals, aligns the shock channel signals using the fiducial point, and generates a template using the aligned shock channel signals. The control system performs other operations, such as those discussed above, as part of a template generation methodology of the present invention. For example, the control system updates the template periodically. By way of further example, the control system updates the template in response to detecting establishment of connectivity between the lead system and the detector system.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
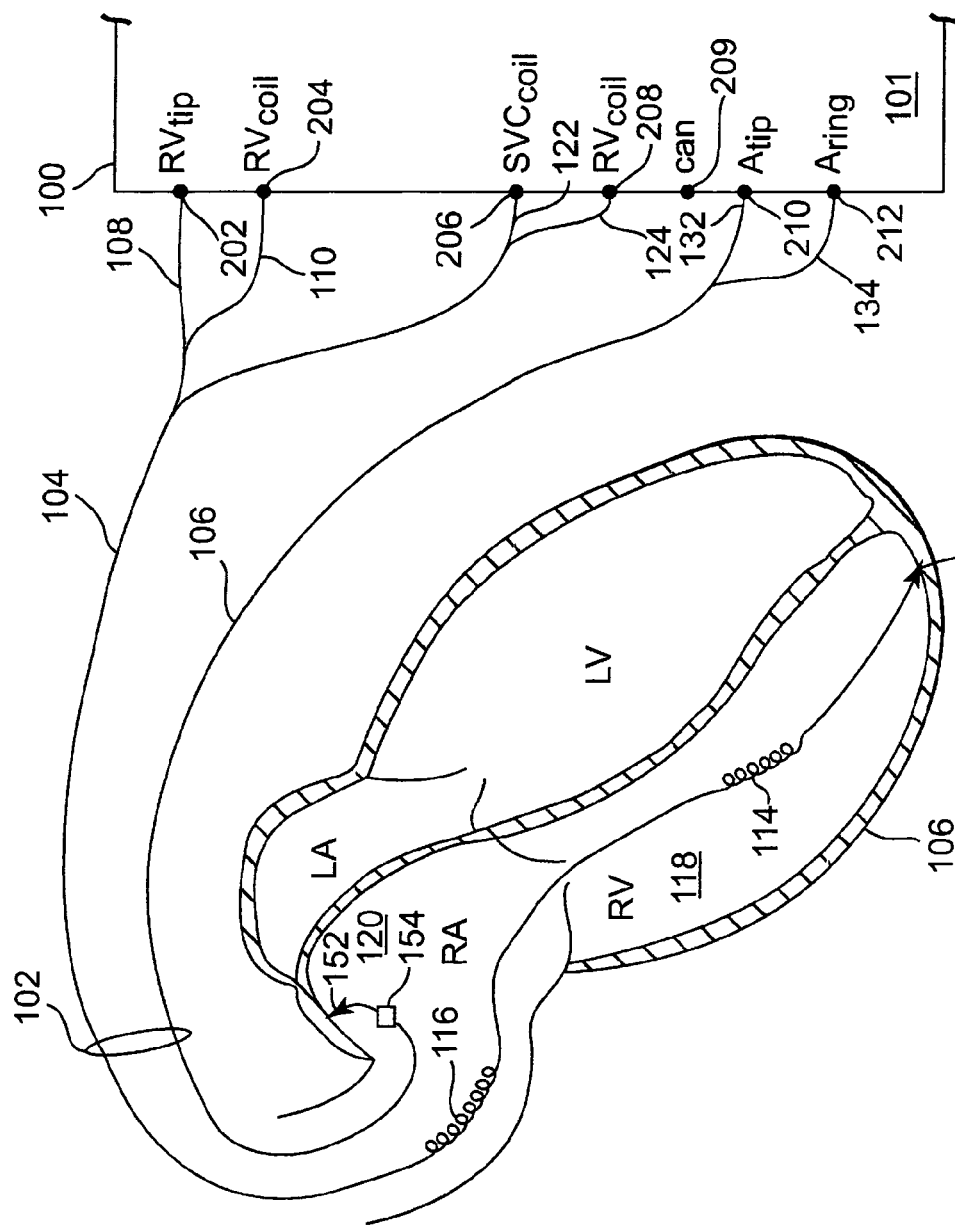
FIG. 1 is a partial view of one embodiment of an implantable medical device with an endocardial lead system extending into atrial and ventricular chambers of a heart.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

The embodiments of the present system illustrated herein are generally described as being implemented in an implantable cardiac defibrillator, which may operate in numerous pacing modes known in the art. The systems and methods of the present invention may also be implemented in other implantable medical devices that sense cardiac activity, such as pacemakers and cardiac monitors, for example.

In one embodiment, an implantable cardiac defibrillator configured as a single chamber defibrillator operates to generate a snapshot representative of one beat of a patient's normal cardiac rhythm in accordance with the principles of the present invention. In another embodiment, an implantable cardiac defibrillator that incorporates the systems and methods of the present invention is a dual chamber defibrillator. Various types of single and multiple chamber implantable cardiac defibrillators are known in the art.

The systems and methods of the present invention may also be implemented in external cardioverter/monitor systems as are known in the art. Also, the present medical system can also be implemented in an implantable atrial cardioverter/defibrillator, which may include numerous pacing modes known in the art. Furthermore, although the present system is described in conjunction with an implantable cardiac defibrillator having a microprocessor-based architecture, it will be understood that the implantable cardiac defibrillator (or other implanted device) may be implemented in any logic-based integrated circuit architecture, if desired.

The present invention provides for systems and methods for monitoring a patient's electrocardiogram and producing a snapshot representative of one of the patient's normal supra-ventricular conducted beats. Producing such a snapshot may be effected at any time for a number of different purposes. By way of example, the diagnosis of a patient's cardiac rhythms may be enhanced by comparing QRS complexes of a current cardiac rhythm to a snapshot of the patient's normal cardiac rhythm produced by employment of the methodologies of the present invention. By way of further example, the titration of drug dosage based on electrocardiographic properties of such a snapshot produced in accordance with the present invention may also be enhanced.

The methodologies of producing an accurate snapshot of a patient's normal cardiac rhythm may be used in combination with an automatic VT/SVT (ventricular tachyarrhythmia/supra-ventricular tachyarrhythmia) rhythm discrimination technique employed in an implantable cardioverter/defibrillator (ICD). Also, the methodologies of the present invention may be used as a component of an automatic Holter analysis system employed in an implantable pacemaker, for example. These and other applications may be enhanced by employment of the systems and methods of the present invention.

Referring now to FIG. 1 of the drawings, there is shown one embodiment of a medical device system which includes an implantable cardiac defibrillator 100 electrically and physically coupled to an intracardiac lead system 102. The intracardiac lead system 102 is implanted in a human body with portions of the intracardiac lead system 102 inserted into a heart 106. The intracardiac lead system 102 is used to detect and analyze electric cardiac signals produced by the heart 106 and to provide electrical energy to the heart 106 under certain predetermined conditions to treat cardiac arrhythmias, including, for example, ventricular fibrillation of the heart 106. In an embodiment in which only monitoring of cardiac activity is performed, the intracardiac lead system 102 need not provide for the production of electrical energy to stimulate the heart 106.

The intracardiac lead system 102 includes one or more pacing electrodes and one or more intracardiac defibrillation electrodes. In the particular embodiment shown in FIG. 1, the intracardiac lead system 102 includes a ventricular lead system 104 and an atrial lead system 106. The ventricular lead system 104 includes an SVC-coil 116, an RV-coil 114, and an RV-tip electrode 112. The RV-coil 114, which is also referred to as an RV-ring electrode, is spaced apart from the RV-tip electrode 112, which is a pacing electrode. In one embodiment, the ventricular lead system 104 is configured as an integrated bipolar pace/shock lead.

The atrial lead system 106 includes an A-tip electrode 152 and an A-ring electrode 154. In one embodiment, the atrial lead system 106 is configured as an atrial J lead.

In this configuration, the intracardiac lead system 102 is positioned within the heart 106, with a portion of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 are positioned at appropriate locations within the right ventricle 118. The SVC-coil 116 is positioned at an appropriate location within the right atrium chamber 120 of the heart 106 or a major vein leading to the right atrium chamber 120 of the heart 106. The RV-coil 114 and SVC-coil 116 depicted in FIG. 1 are defibrillation electrodes.

Additional pacing and defibrillation electrodes can also be included on the intracardiac lead system 102 to allow for various bipolar sensing, pacing, and defibrillation capabilities. For example, the intracardiac lead system 102 may include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Other intracardiac lead and electrode arrangements and configurations known in the art are also possible and considered to be within the scope of the present system.

The ventricular and atrial lead systems 104, 106 include conductors for communicating sense, pacing, and defibrillation signals between the cardiac defibrillator 100 and the electrodes and coils of the lead systems 104, 106. As is shown in FIG. 1, ventricular lead system 104 includes a conductor 108 for transmitting sense and pacing signals between the RV-tip electrode 112 and an RV-tip terminal 202 within the cardiac defibrillator 100. A conductor 110 of the ventricular lead system 104 transmits sense signals between the RV-coil or ring electrode 114 and an RV-coil terminal 204 within the cardiac defibrillator 100. The ventricular lead system 104 also includes conductors 122, 124 for transmitting sense and defibrillation signals between terminals 206, 208 of the cardiac defibrillator 100 and SVC- and RV-coils 116 and 114, respectively. The atrial lead system 106 includes conductors 132, 134 for transmitting sense and pacing signals between terminals 210, 212 of the cardiac defibrillator 100 and A-tip and A-ring electrodes 152 and 154, respectively.

Figure 2:
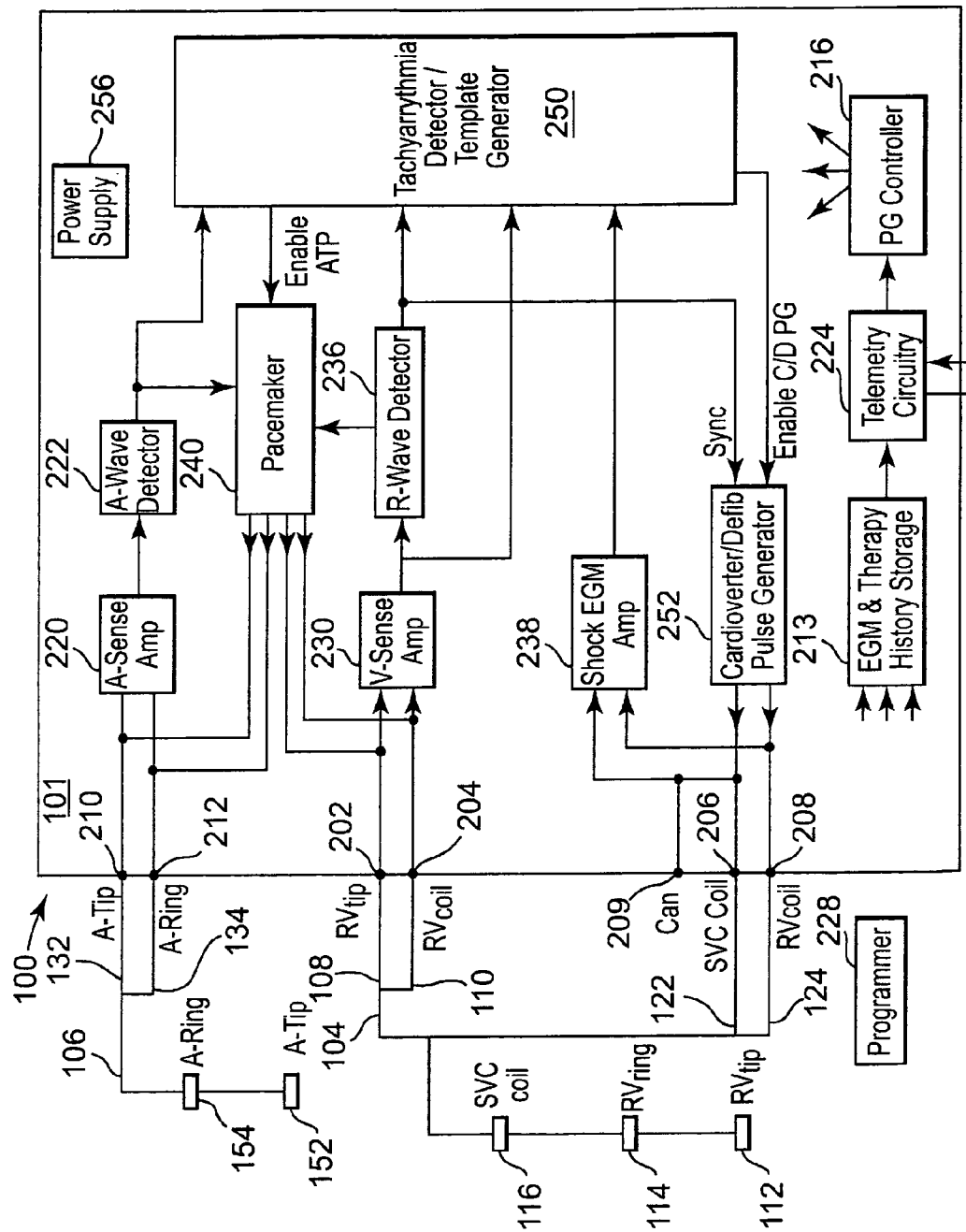
FIG. 2 is a block diagram of a cardiac defibrillator with which a template generation methodology of the present invention is implemented.

Referring now to FIG. 2, there is shown an embodiment of a cardiac defibrillator 100 suitable for implementing a normal cardiac rhythm template generation methodology of the present invention. The cardiac defibrillator 100 includes control system circuitry 101 for receiving cardiac signals from a heart 106 and delivering electrical energy to the heart 106. The control system circuitry 101 includes terminals 202, 204, 206, 208, 209, 210, and 212 for connecting to the electrodes and coils of the intracardiac lead system 102, as previously discussed.

In one embodiment, the control system circuitry 101 of the cardiac defibrillator 100 is encased and hermetically sealed in a housing 130 suitable for implanting in a human body as is known in the art. Power to the cardiac defibrillator 100 is supplied by an electrochemical battery 256 that is housed within the cardiac defibrillator 100. A connector block (not shown) is additionally attached to the housing 130 of the cardiac defibrillator 100 to allow for the physical and electrical attachment of the intracardiac lead system conductors to the cardiac defibrillator 100 and the encased control system circuitry 101.

In one embodiment, the control system circuitry 101 of the cardiac defibrillator 100 is a programmable microprocessor-based system, with a controller 216 and a memory circuit (not shown). The memory circuit contains parameters for various pacing, defibrillation, and sensing modes and stores data indicative of cardiac signals received by the control system circuitry 101. The controller 216 and memory circuit cooperate with other components of the control system circuitry 101 to perform operations involving the generation of a template representing a snapshot of one beat of a patient's normal cardiac rhythm according to the principles of the present invention, in addition to other sensing, pacing and defibrillation functions. A memory 213 is also provided for storing historical EGM and therapy data, which may be used onboard for various purposes and transmitted to an external programmer unit 228 as needed or desired.

Telemetry circuitry 224 is additionally coupled to the control system circuitry 101 to allow the cardiac defibrillator 100 to communicate with an external programmer unit 228. In one embodiment, the telemetry circuitry 224 and the programmer unit 228 use a wire loop antenna and a radio frequency telemetric link, as is known in the art, to receive and transmit signals and data between the programmer unit 228 and the control system circuitry 101. In this manner, programming commands and instructions are transferred to the controller 216 of the cardiac defibrillator 100 from the programmer unit 228 during and after implant, and stored cardiac data pertaining to sensed arrhythmic episodes within the heart 106, template information, and subsequent therapy or therapies applied to correct the sensed arrhythmic event are transferred to the programmer unit 228 from the cardiac defibrillator 100, for example.

Cardiac signals sensed through use of the RV-tip electrode 112 are near-field signals or rate channel signals as are known in the art. More particularly, a rate channel signal is detected as a voltage developed between the RV-tip electrode 112 and the RV-coil 114. Rate channel signals developed between the RV-tip electrode 112 and the RV-coil 114 are referred to herein as rate channel signals or signals measured from the rate channel.

Cardiac signals sensed through use of one or both of the defibrillation coils or electrodes 114, 116 are far-field signals, also referred to as morphology or shock channel signals, as are known in the art. More particularly, a shock channel signal is detected as a voltage developed between the RV-coil 114 and the SVC-coil 116. A shock channel signal may also be detected as a voltage developed between the RV-coil 114 and the SVC-coil 116 and can electrode 209. A shock channel signal may further be detected as a voltage developed between the RV-coil 114 and the can electrode 209. Shock channel signals developed using appropriate combinations of the RV-coil, SVC-coil, and can electrodes 114, 116 and 209 are sensed and amplified by a shock EGM amplifier 238, the output of which is coupled to the tachyarrythmia detector 250.

In the embodiment of the cardiac defibrillator 100 depicted in FIG. 2, RV-tip and RV-coil electrodes 112, 114 are shown coupled to a V-sense amplifier 230. Rate channel signals received by the V-sense amplifier 230 are communicated to an R-wave detector 236. The R-wave detector 236 serves to sense and amplify the rate channel signals (e.g., R-waves) and communicate the detected signals to a pacemaker 240 and a tachyarrhythmia detector 250.

A-tip and A-ring electrodes 152, 154 are shown coupled to an A-sense amplifier 220. Atrial sense signals received by the A-sense amplifier 220 are communicated to an A-wave detector 222, which serves to sense and amplify the A-wave signals. The atrial signals are communicated from the A-wave detector 222 to the pacemaker 240 and the tachyarrhythmia detector 250. The pacemaker 240 communicates pacing signals to the RV-tip and A-tip electrodes 112 and 152 according to a preestablished pacing regimen under appropriate conditions. Blanking circuitry (not shown) is employed in a known manner when a ventricular or atrial pacing pulse is delivered, such that the ventricular channel, atrial channel, and shock channel are properly blanked at the appropriate time and for the appropriate duration.

The cardiac defibrillator 100 depicted in FIG. 1 is well-suited for implementing a template generation methodology according to the principles of the present invention. In the embodiment show in FIG. 1, the template generation processes of the present invention are carried out by the tachyarrhythmia detector/template generator 250. The shock channel and rate channel signals used for template generation and related template operations are provided by the shock EGM amplifier 238 and the V-sense amplifier 230, respectively. It is understood that the required shock and rate channel signals may be developed and processed by components other than those depicted in FIG. 1 for system architectures that differ from that described herein.

In general terms, a template refers to a set of points, called features, which describes a representative waveform of atrial origin as measured from the shock channel, together with the predominate fiducial point polarity of the same waveform. The fiducial point is derived from the rate channel.

The number of points or features that define a template is preferably a set of is eight points, but may vary. The features are used to compare other template beats with the reference template. The more correlated a beat is with the template, the higher the likelihood that the beat is of atrial origin. It is noted that the term "correlate" in this context means that a feature correlation coefficient (FCC), the square of the correlation coefficient, exceeds a given constant. It is further noted that the processes and calculations discussed herein do not imply a specific design, hardware or software architecture or implementation.

The template is updated periodically after initial template generation. When a template update is initiated, the current rhythm is checked for rate and beat regularity. If the rhythm rate and regularity satisfy certain criteria, the stored template is checked for correlation with the current template beats. If the current SVR (supra-ventricular rhythm) morphology has changed sufficiently from that of the stored template, a new candidate template is generated to potentially replace the stored template, as will be discussed below in greater detail.

Figure 3:
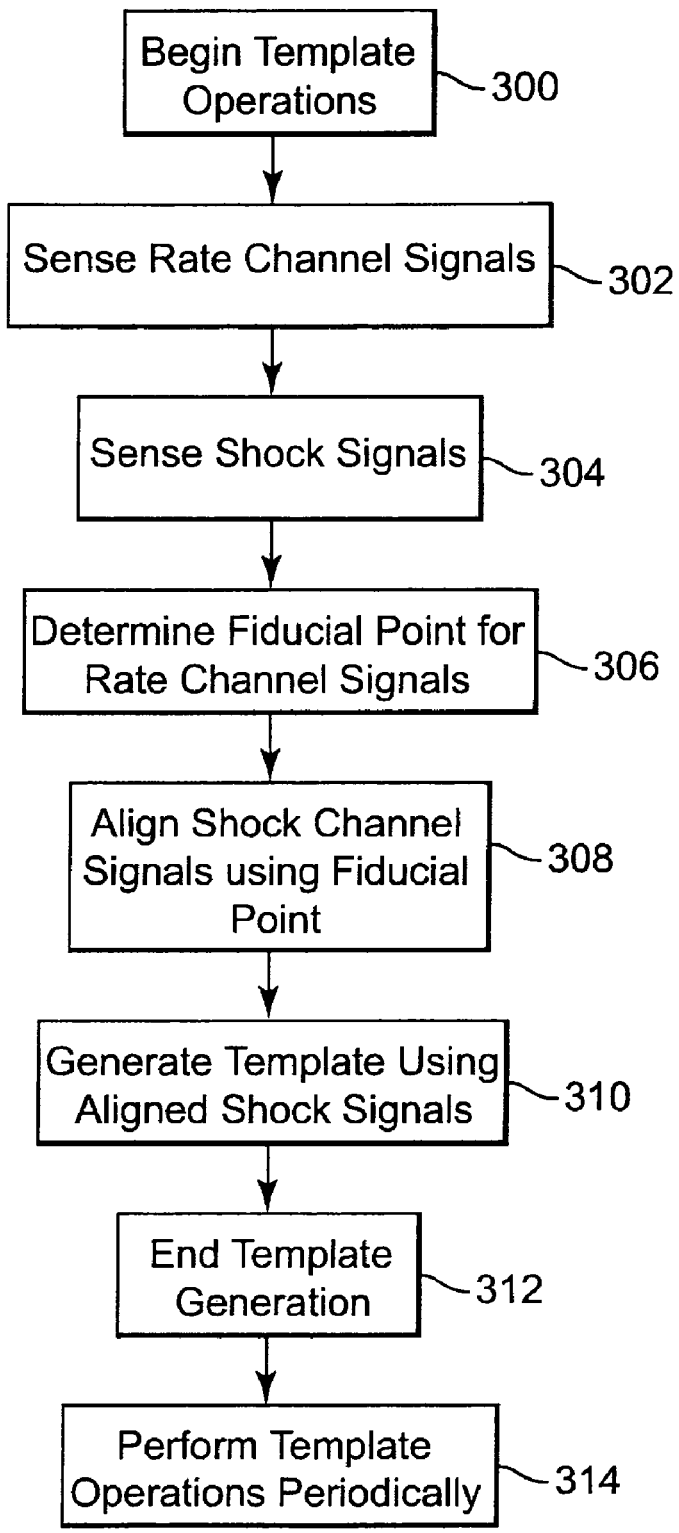
FIG. 3 illustrates a number of steps associated with shock channel template generation in accordance with an embodiment of the present invention.

Turning now to FIG. 3, there is illustrated various processes involving the production of a snapshot representative of one beat of a patient's normal cardiac rhythm according to an embodiment of the present invention. A template is generated through multiple stages and may be regenerated or updated periodically as needed or desired. Upon initiation 300 of template operations, rate channel signals, which constitute near-field signals, are sensed 302. Shock channel signals, which constitute far-field signals, are also sensed 304. A fiducial point for the rate channel signals is determined 306. The shock channel waveforms are then aligned 308 using the fiducial point developed from the rate channel signals. A template is generated 310 using the aligned shock channel waveforms. The template generation procedure is then completed 312. The template may be updated 314 periodically as needed or desired, which involves comparing the currently stored template with subsequently received template beats on a beat-by-beat basis.

Figure 4:
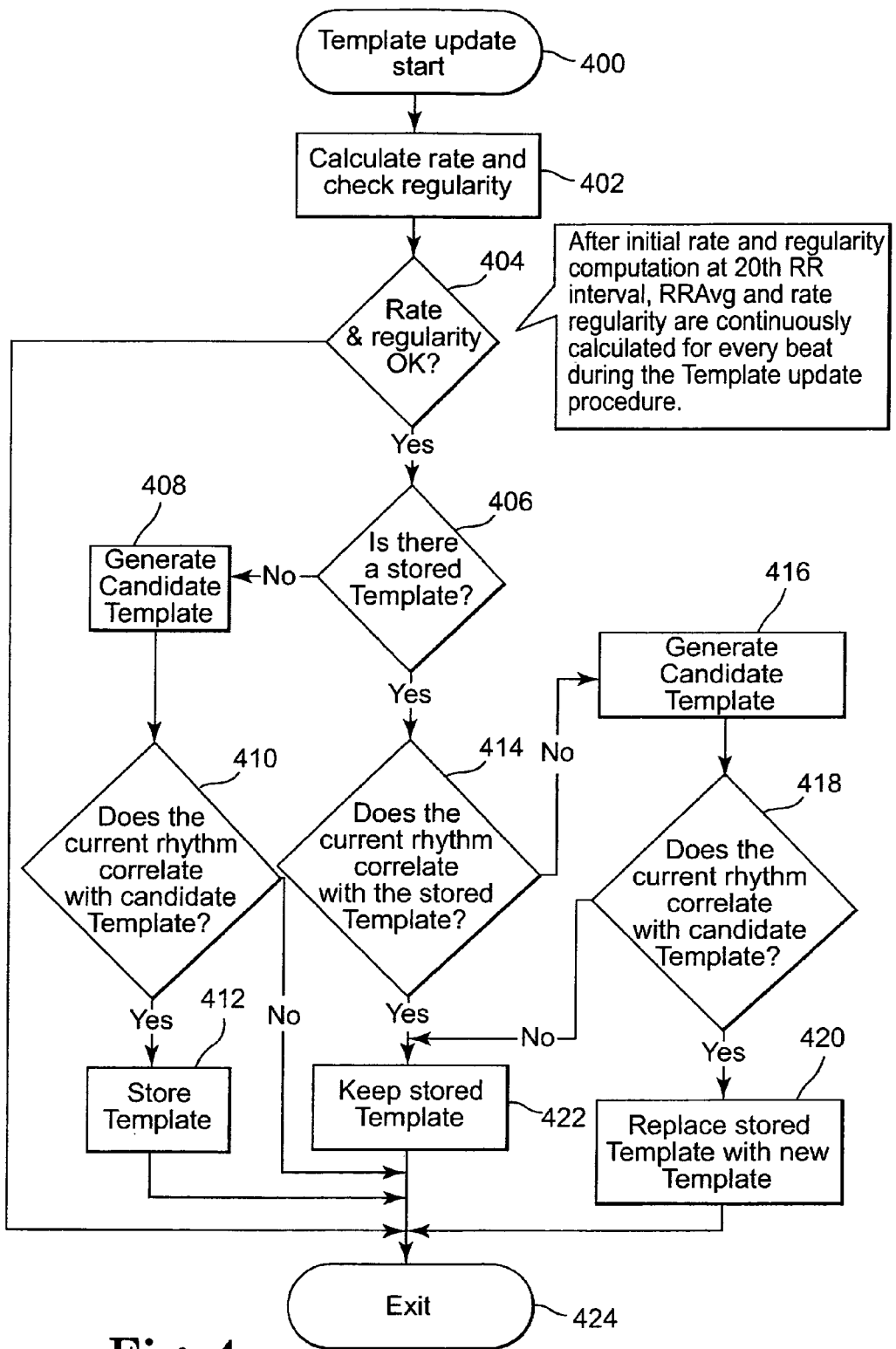
FIG. 4 illustrates various steps associated with shock channel template generation in accordance with an embodiment of the present invention.

FIG. 4 illustrates various processes of an automatic template update procedure in accordance with an embodiment of the present invention. According to this embodiment, upon initiation 400 of a template update procedure, the rate and regularity of sensed R-waves are calculated 402. During the template update procedure, the rate and regularity are repeatedly calculated and checked for "normalcy" with respect to predefined criteria, as will be described in greater detail below.

For example, after the initial rate and regularity computations are performed at the $20^{th}$ RR interval, the RR average interval and rate regularity are continuously calculated for every beat during the template update procedure. If the rate and regularity are acceptable 404, a check is made to determine 406 whether there exists a stored template. If not, a candidate template is generated 408. The current rhythm is compared with the candidate template. If the current rhythm correlates with the candidate template 410, the candidate template is stored 412 as the current template. If the current rhythm does not correlate with the candidate template 410, the candidate template is discarded and the template update procedure is terminated 424 and subsequently reinitiated in accordance with programming.

If there exists a stored template 406, a check is made to determine if the current rhythm correlates with the stored template 414. If the current rhythm correlates with the stored template, the stored template is retained 422 and the template update procedure is terminated 424 and subsequently reinitiated in accordance with programming. If, however, the current rhythm does not correlate with the stored template 414, a candidate template is generated 416. If the current rhythm correlates with the candidate template 418, the stored template is replaced 420 with the newly generated candidate template, and the template update procedure is terminated 424 and subsequently reinitiated in accordance with programming. If, however, the current rhythm does not correlate with the candidate template 418, the currently stored template is retained 422, and the template update procedure is terminated 424 and subsequently reinitiated in accordance with programming.

Figure 5:
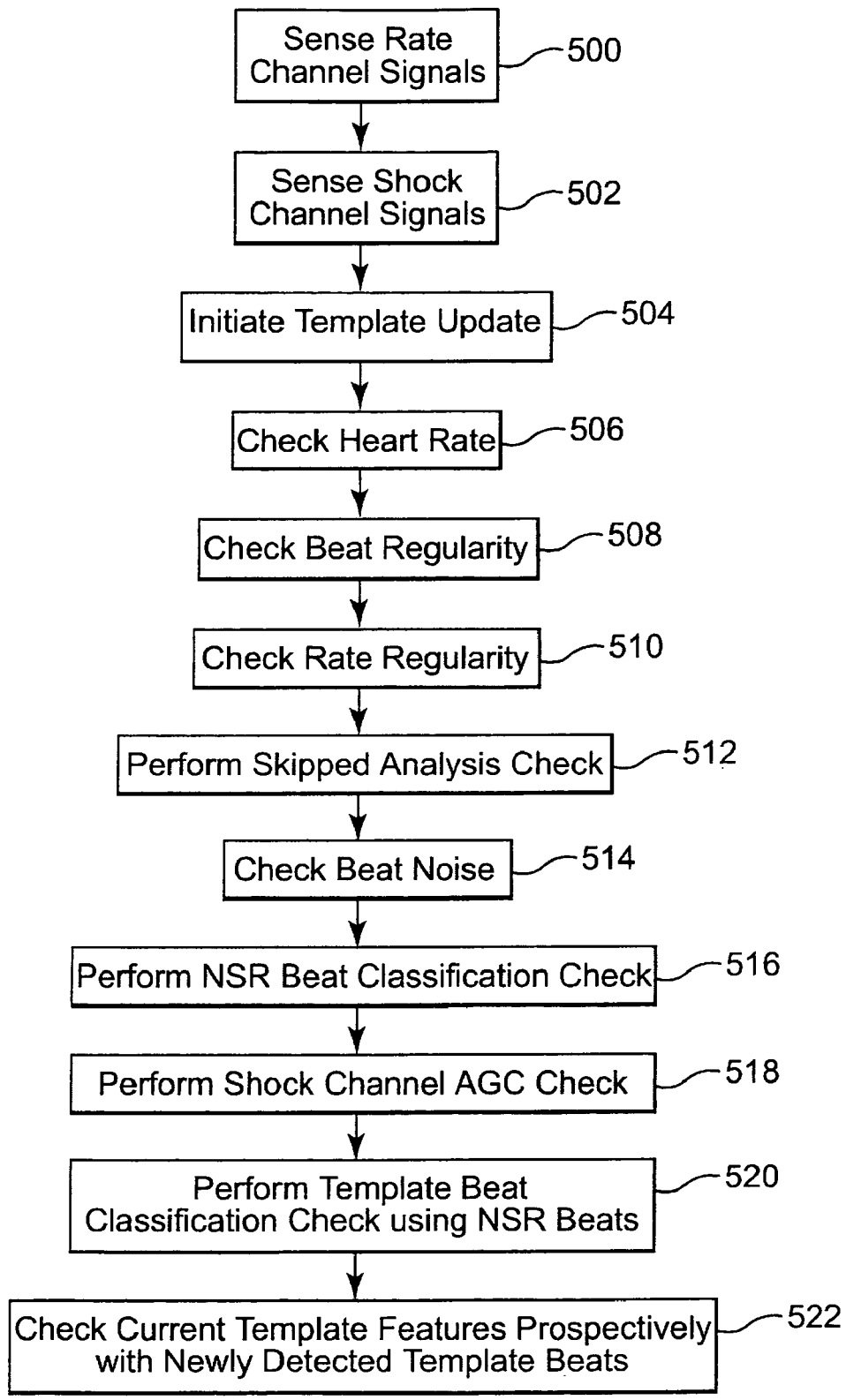
FIG. 5 is a more detailed illustration of various steps associated with shock channel template generation in accordance with an embodiment of the present invention.
Figure 6:
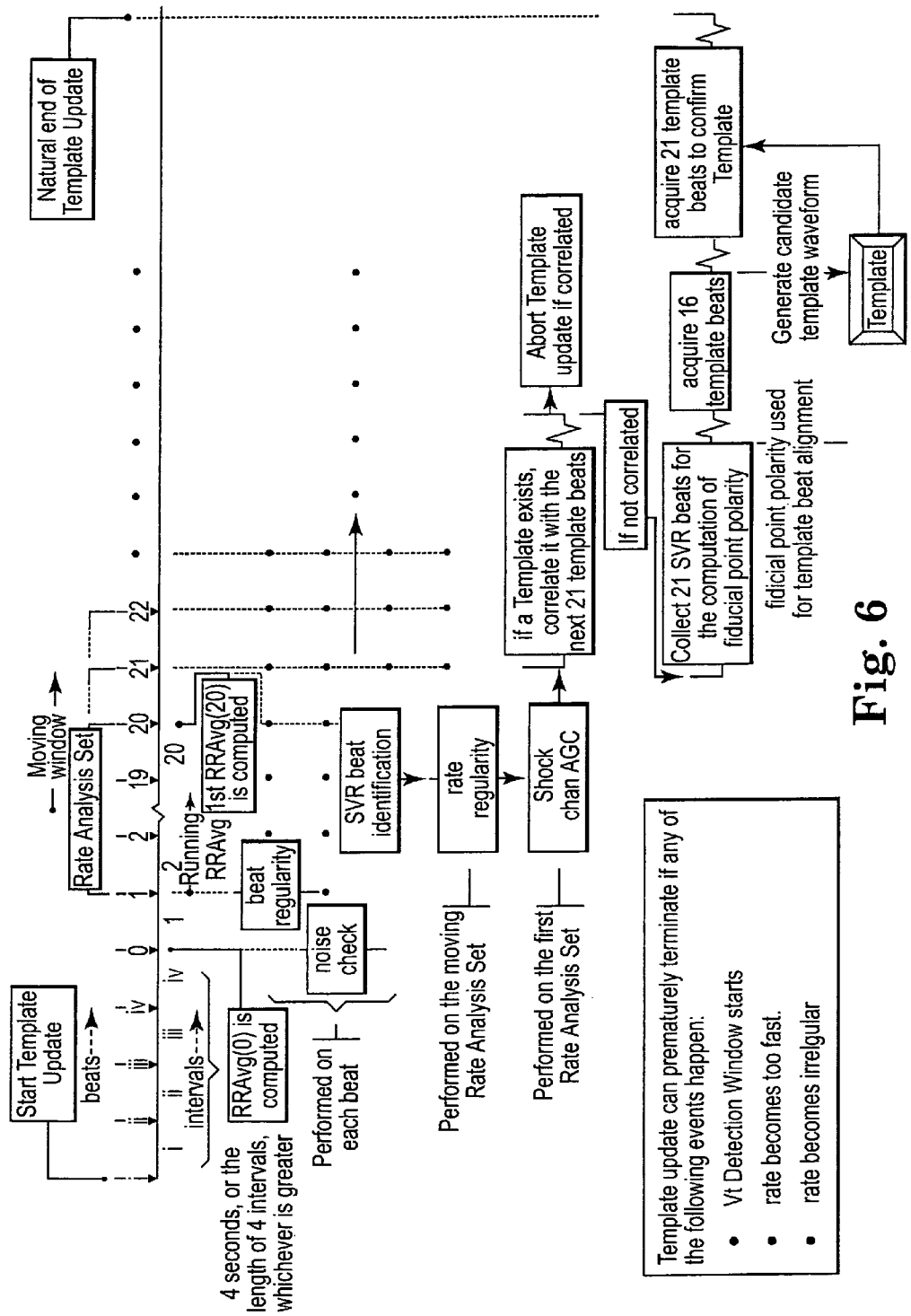
FIG. 6 illustrates details of the various steps shown in FIG. 5 in a linear time fashion.

Referring now to FIG. 5, a number of additional template generation processes will now be described. FIG. 6 depicts these and other template generation processes in a linear time fashion according to an embodiment of the present invention. Rate and shock channel signals are sensed 500, 502 in a manner described previously.

Template update operations are initiated 504 and terminated according to programming and under certain conditions. The template update time period is programmable, such as in a range of 10 minutes to 24 hours, with 10-minute increments, for example. The nominal value is 120 minutes. The update time period is typically not a user programmable parameter.

A template update is initiated 504 when one of several initiating events occurs. For example, a template update may be initiated in response to certain mode switching, such as when the cardiac defibrillator is programmed from Off mode to Monitor or Monitor-plus-Therapy mode, or from Monitor mode to Monitor-plus-Therapy mode, or tachyarrhythmia discrimination programming is programmed from OFF to ON. A template update may be initiated upon detecting connectivity between the cardiac defibrillator and implanted leads when the leads are connected to the defibrillator. In a preferred embodiment, a template update can be initiated by the clinical user via an external programmer.

A template update is also initiated when a scheduled update time arrives and the previous update is finished. An update timer restarts when one of several events occurs. A template update is manually initiated by changing the mode as described in the preceding paragraph. A template update is initiated in response to expiration of the update timer.

A template update is immediately aborted under certain conditions, such as: onset of ventricular tachycardia (VT); expiration of the update timer while the VT is active; or the update timer expires while the post therapy timer is not expired. For example, a template update is aborted in response to delivery of a therapy. Such therapies include, for example, any induction attempt or tachyarrhythmia therapy delivery, such as Fib Hi, Fib Lo, Shock on T, Ventricular PES, Ventricular burst pacing, Ventricular ATP, and Ventricular therapy shock.

After initiating 504 a template update, heart rate and regularity are checked 506, 508. RR intervals are developed from the sensed rate channel signals. An RR interval is measured as an interval between Vs to Vs, Vs to Vp, Vp to Vs, or Vp to Vp events, where Vs is the ventricular sensed event detection time and Vp is the ventricular pace pulse delivery time.

The initial RR average (RRavg) is calculated as the average of the first four RR intervals. The RRavg is calculated as a running average as is characterized in Equation [1] below:

$$RRavg(I) = 0.875 * RRavg(I-1) + 0.125 * RR(I) \quad [1]$$

where, RR(I) is the current RR interval and RRavg(0) is the initial RR average.

When the 20th RR interval after the initial RR average computation is acquired, RRavg(20) is compared to a rate threshold. If the heart rate is too fast, then the template update is suspended until the next scheduled template update time. According to one configuration, the rate is defined as too fast if RRavg is less than an interval corresponding to the smaller of 110 bpm or 5 bpm below the lowest tachyarrhythmia threshold.

A beat is classified as a "regular" beat when an RR interval is larger than 87.5% and less than 125% of the RRavg. The first regular beat is available only after initial RRavg is calculated.

Heart rate is classified as "regular" if at least 50% of the beats are regular. According to one approach, after the $20^{th}$ RR interval is acquired, heart rate regularity is checked. If the rate is not regular, the template update is suspended until the next scheduled template update time.

After initial rate and regularity computations are completed at the 20th RR interval, the RRavg and rate regularity are continuously calculated for every beat during the template update procedure. A 20 RR interval moving window is used when is rate regularity is continuously calculated. If the rate becomes too high or the rate becomes irregular at any stage of the template update procedure, the template update is suspended immediately and reinitiated at the next update time.

If a subsequently sensed beat is detected before the analysis of a current beat is finished, the analysis of the subsequent beat can be optionally skipped 512. The number of analysis skipped beats of the latest 20 beats is continuously counted. If the number of analysis skipped beats is greater than 4, then the template update is suspended immediately until the next update time. However, it is preferable that every RR interval is calculated and used to update the RRavg and rate regularity computations. If RRavg or rate regularity is not updated at any RR interval, the template update is suspended immediately until the next update time.

A noise check algorithm is initiated 514 after the initial RR average is computed. The noise level, for example, may be measured in the ST segment or PR segment of the shock channel. By way of example, the PR noise window may be set to 100 ms in duration starting at the fiducial point minus 150 ms. The PR noise level is measured as the absolute maximum peak value in the PR noise window. If the noise level is too high, such as greater than 20% of the R-wave peak, for example, then an excessively noisy condition is indicated. The ST noise window may be 100 ms in duration starting 100 ms at the fiducial point plus 150 ms. The noise level is measured as the number of baseline crossings in the ST noise window. If the number of baseline crossings is excessively large, such as greater than 5, for example, then an excessively noisy condition is indicated.

If multiple events of the rate channel are triggered in short intervals, and the width of the beats exceeds 200 ms, then the rate channel is classified as noisy. If the rate channel is classified as noisy, then the beat is classified as a noisy beat.

A beat satisfying all of the following conditions is classified 516 as an NSR beat: 1) the largest amplitude of a beat sensed from the rate channel is larger than 50% of the maximum ADC (analog-to-digital converter) value; 2) the beat is not a ventricular paced beat and the previous beat is not a ventricular paced beat; 3) the beat is a regular beat as defined hereinabove; 4) the beat is not noisy as defined hereinabove; and 5) the beat is not an analysis skipped beat as defined hereinabove.

An automatic gain control (AGC) check is performed 518 on the shock channel. The shock channel AGC procedure involves measuring the amplitude of an NSR beat sensed from the shock channel from a window starting 100 ms before Vs, with a duration of 200 ms if there is no atrial pacing pulse within an applicable tachyarrhythmia discrimination detection window. When the 20$^{th}$ beat is acquired for rate and rate regularity computations, the average peak is computed.

If the number of NSR beats is less than 11, the update is suspended until the next scheduled template update time. The shock channel gain is adjusted to an available gain that sets the average peak nearest to 60% of the maximum ADC value. For example, if the average peak amplitude of the NSR beats does not fall within a specified range, such as 30% to 70% of a specified maximum value, then the gain of the shock channel is adjusted to an available gain that sets the average peak amplitude nearest to 60% of the maximum ADC value.

An NSR beat that meets all of the following additional conditions is classified 520 as a template beat that is used to form a new template or to confirm a template. Template beats are classified only if there is a defined fiducial point type. The additional conditions are: 1) the amplitude of the fiducial point is larger than 50% of the maximum ADC value; 2) the saturated fiducial point (i.e., a point with either the maximum positive or maximum negative ADC value) is not followed by another saturated sample on the rate channel; 3) the shock channel beat amplitude is not less than 40% or greater than 90% of the maximum ADC value; 4) the following Vs is not detected within the applicable tachyarrhythmia discrimination detection window; and 5) an atrial pacing pulse does not occur within the applicable tachyarrhythmia discrimination detection window.

After shock channel AGC is performed, and if there are stored template features, the currently stored template features are checked 522 prospectively with newly detected template beats. This is a beat-by-beat operation, and there is no need to store multiple beats.

The fiducial point type of the current template features is used for time alignment. If at least 10 beats out of 21 template beats have FCC values larger than a preestablished FCC threshold (e.g., an FCC value of 0.95), then the currently stored template features are sufficiently representative of the template beats, and the template update is suspended until the next scheduled template update time. Otherwise, generation of new template features is attempted to replace the currently stored template features. If it is required to collect more than 50 analyzed beats to obtain 21 template beats, the update is aborted until the next scheduled template update time.

Figure 7:
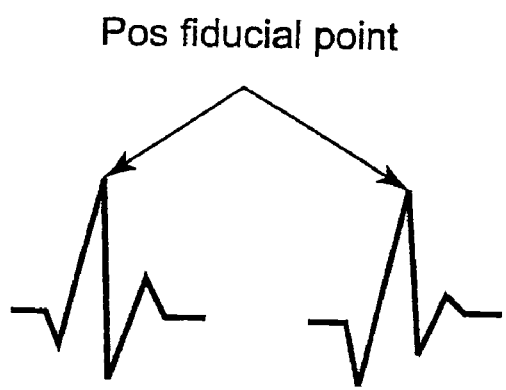
FIGS. 7 and 8 respectively illustrate positive and negative type fiducial points determined from rate channel signals in accordance with the principles of the present invention.
Figure 8:
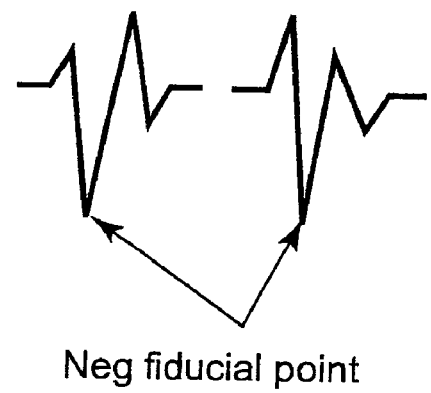

As discussed previously, a template is generated using a fiducial point developed from rate channel signals for purposes of shock channel waveform alignment. The fiducial point type is either positive (Pos) or negative (Neg). The positive peak (Pos) and negative peak (Neg) of a sensed beat detected on the rate channel determines the fiducial point type. FIGS. 7 and 8 depict positive and negative fiducial point types, respectively. The Pos and Neg peaks are measured as absolute values. For each NSR beat, the positive peak (Pos) and negative peak (Neg) are measured from a window starting at Vs, with a duration of 100 ms. The fiducial point type of a beat is determined as follows:

If Pos>0.9*Neg, the fiducial point type is Pos

Otherwise, the fiducial point type is Neg

After shock channel AGC is performed, the fiducial point type of each NSR beat is evaluated. After 21 fiducial point types are evaluated, majority rule is applied to determine the fiducial point type for alignment. If it takes more than 50 analyzed beats to acquire 21 fiducial types, the template update is suspended until the next scheduled template update time.

Figure 9:
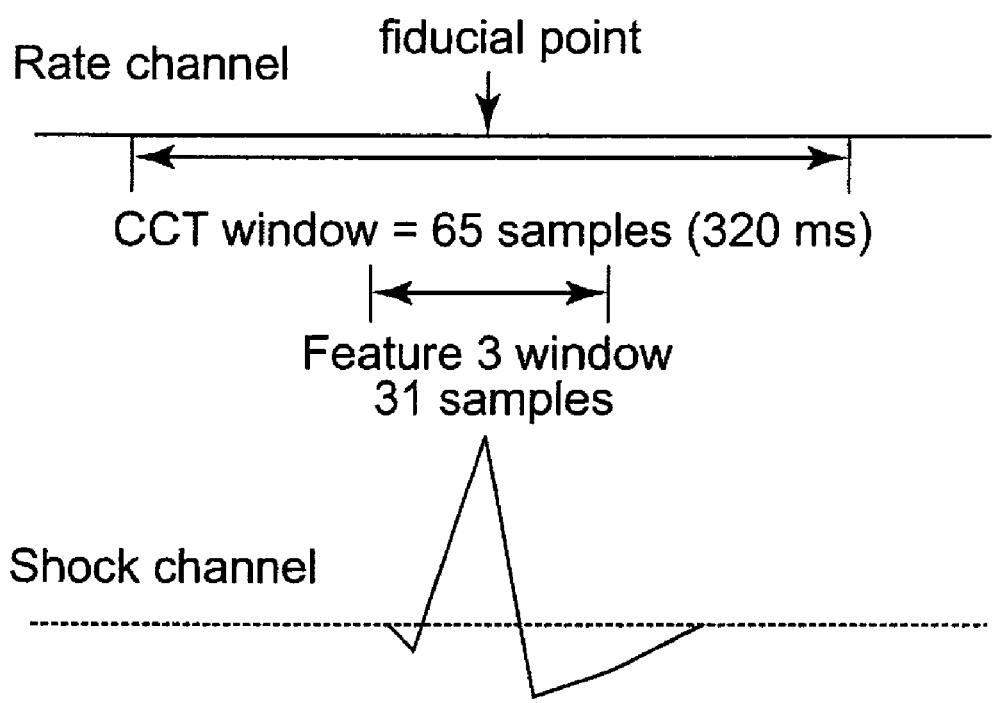
FIG. 9 illustrates alignment of shock channel waveforms with respect to a fiducial point determined from rate channel signals in accordance with the principles of the present invention.

The shock channel waveforms of template beats are aligned within the aforementioned tachyarrhythmia discrimination detection window using the new fiducial point developed from rate channel signals. In one embodiment, and as depicted in FIG. 9, the tachyarrhythmia discrimination detection window consists of 65 samples centered at the fiducial point which are used for template generation. The template waveform is generated using point-by-point averaging of 16 template beats. In particular, 16 samples acquired from the same time location of aligned 16 template beats are averaged or median filtered to generate a sample of the template waveform. For example, the template waveform(i) may be characterized by Equation [2] below:

$$\text{Template Waveform}(i) = \frac{1}{16}\sum_{j=1}^{16} \text{Template Beat}(i, j) \quad [2]$$

where, the term template beat (i,j) is the i$^{th}$ sample from the detection window of the j$^{th}$ template beat. If more than 50 analyzed beats are required to obtain 16 template beats, the template update is aborted and rescheduled.

Figure 10:
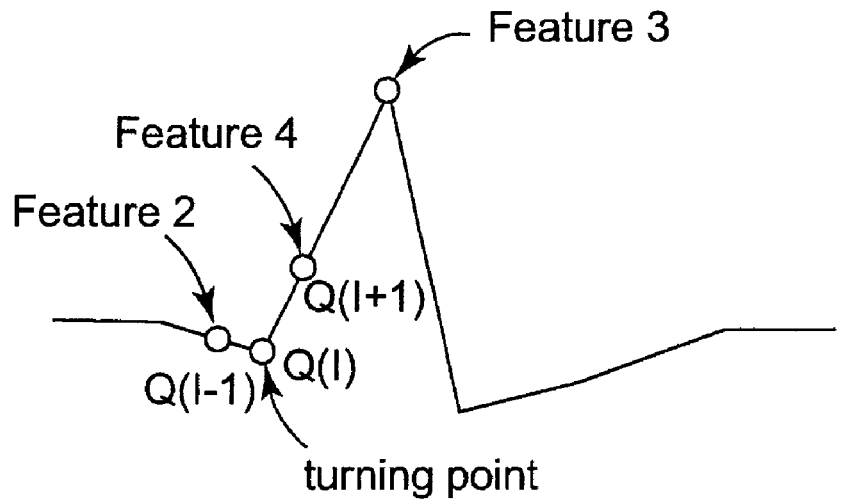
FIGS. 10 and 11 show morphological features, including turning point and flat slope features, respectively, selected in accordance with the principles of the present invention.
Figure 11:
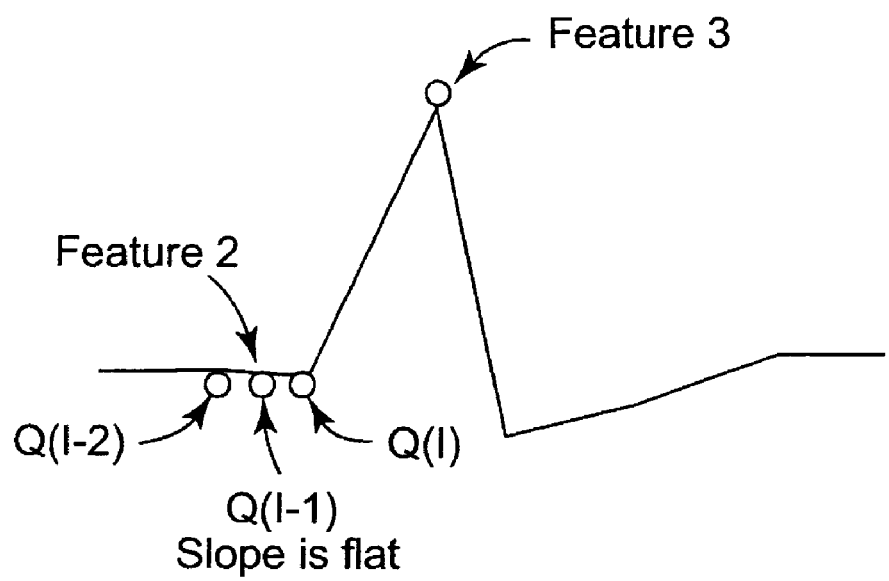

According to an embodiment of the present invention, and with reference to FIGS. 10 and 11, five features are initially selected for the shock channel template, followed by three additional features determined at midpoints between certain ones of the five selected features. The five features of the template are determined in the following manner.

Feature 3 is selected as the absolute maximum peak in a feature window defined by 31 samples centered at the fiducial point. If the positive peak amplitude is equal to the negative peak amplitude, the positive peak is selected as Feature 3.

Feature 2 is found by searching backward from Feature 3 until a point is reached that meets the following conditions: 1) the search is limited to 10 samples. If no point satisfies the following conditions, then the 10th sample becomes Feature 2; 2) the amplitude is less than 25% of the maximum peak; and 3) a turning point is found or the slope is flat.

By way of example, let Q(I) represent the current sample. A turning point is found if:

$Q(I-1) > Q(I)$ and $Q(I) < Q(I+1)$ for a positive Feature 3

$Q(I-1) < Q(I)$ and $Q(I) > Q(I+1)$ for a negative Feature 3

As is shown in FIG. 10, Q(I−1) is selected as Feature 2. As such, Feature 2 is selected as a turning point.

The slope is considered flat, as shown in FIG. 11, if abs(Q(I)−Q(I−1))<4 and abs(Q(I)−Q(I−2))<4, in the case when the ADC maximum value is 128. In the illustrative depiction of FIG. 11, Q(I−1) is selected as Feature 2. As such, Feature 2 is selected as a flat slope point.

Feature 4 is found by searching forward starting from Feature 3 until a point is reached that meets the following conditions: 1) the search is limited to 10 samples. If no point satisfies the following conditions, then the 10th sample becomes Feature 4; 2) the amplitude is less than 25% of the maximum peak; and 3) a turning point is found or the slope is flat.

By way of example, let Q(I) represent the current sample. A turning point is found if:

$Q(I+1) > Q(I)$ and $Q(I) < Q(I-1)$ for a positive Feature 3

$Q(I+1) < Q(I)$ and $Q(I) > Q(I-1)$ for a negative Feature 3

Q(I+1) is selected as Feature 4, as is shown in FIG. 10. The slope is flat if abs(Q(I)−Q(I+1))<4 and abs(Q(I)−Q(I+2))<4. In this case, Q(I+1) is selected as Feature 4.

Feature 1 is selected as the seventeenth sample from the beginning of the detection window. Feature 5 is selected as the last sample of the detection window. Three additional features are selected at the midpoint of Features 1 and 2, the midpoint of Features 2 and 3, and the midpoint of Features 3 and 4, respectively. If a midpoint falls between two sample points, the leftmost (earlier in time) point is selected. Thus, according to this embodiment, eight feature values (e.g., amplitudes) and their associated locations with respect to the fiducial point and the corresponding fiducial point type are saved for beat classification.

The new template features are confirmed prospectively with newly detected template beats. As discussed previously, this confirmation processes is performed on a beat-by-beat basis, such that there is no need to store template data for multiple beats.

In one particular embodiment, Equation [3], provided below, is used to compute the feature correlation coefficient (FCC) between template features and beat features to be classified:

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [3]$$

where, Xi represents template N features and Yi represents beat N features, and N=8 in this illustrative example. The sign of the numerator term $$N\sum_{i=1}^{N} X_i Y_i - \left(\sum_{i=1}^{N} X_i\right)\left(\sum_{i=1}^{N} Y_i\right)$$

is checked before squaring. If the numerator is negative, the beat is uncorrelated, and the remainder of the computation need not be performed.

If at least 10 beats out of 21 template beats have an FCC greater than the FCC threshold (e.g., 0.95), the new template features replace the currently stored template features. Otherwise, the new template features do not sufficiently represent the new template beats, and the currently stored template features are kept until the next scheduled template update time. If it is required to collect more than 50 analyzed beats to obtain 21 template beats, the template update is suspended until the next scheduled template update time.

Figure 12A:
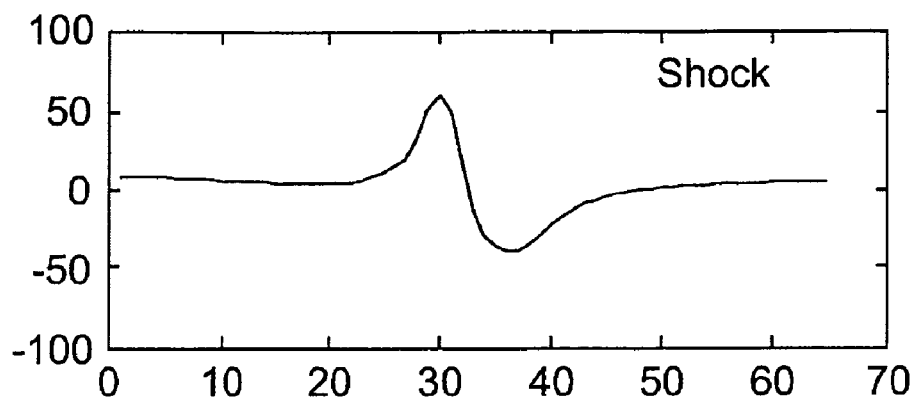
FIGS. 12A-12B illustrate shock and rate waveforms generated in accordance with the principles of the present invention.
Figure 12B:
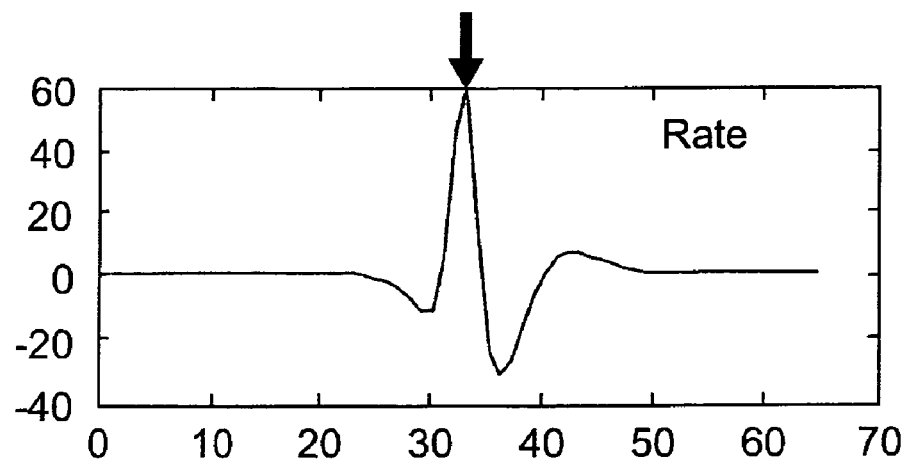

For purposes of illustration, and not of limitation, FIGS. 12-16 show shock and rate channel waveforms associated with various stages of a template generation methodology of the present invention. In FIG. 12, there is illustrated a shock channel template, shown as FIG. 12A, and a rate channel waveform of a positive fiducial point type, shown as FIG. 12B. The shock and rate waveforms depicted in is FIGS. 12A and 12B are developed in a manner previously described.

Figure 13A:
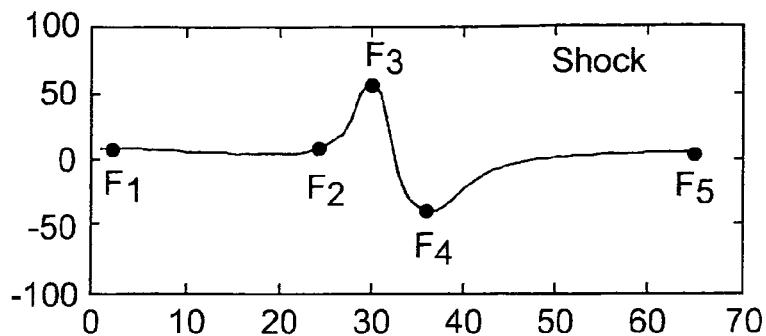
FIGS. 13A-13B illustrate shock and rate waveforms of the present invention, with the shock template including a number of selected morphological features.
Figure 13B:
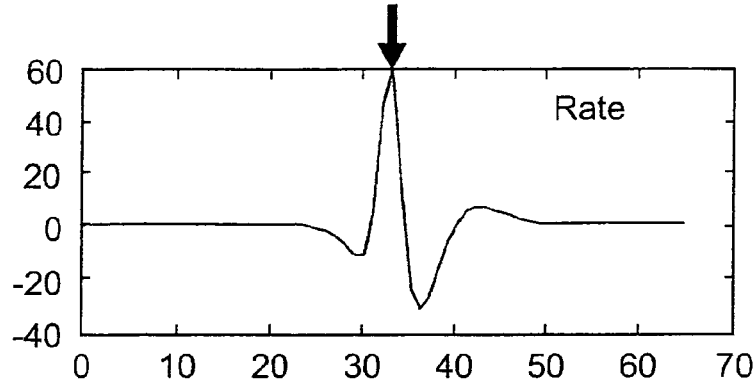
Figure 14A:
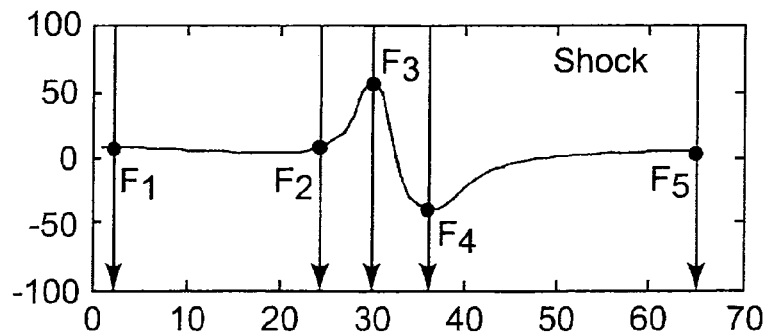
FIGS. 14A-14B illustrate shock and rate waveforms of the present invention, with amplitude and location information associated with selected morphological features.
Figure 14B:
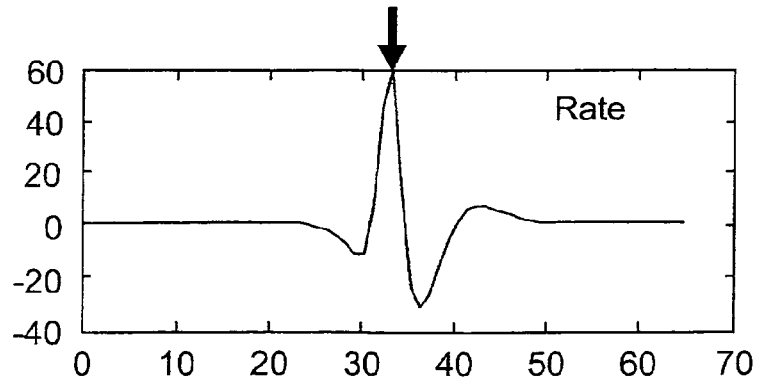

FIGS. 13A and 13B reiterate the shock and rate waveforms of FIGS. 12A and 12B, respectively. In addition, FIG. 13A illustrates five features that have been initially selected for performing FCC computations. According to this embodiment, feature $F_3$ of the shock channel template shown in FIG. 13A is selected as the absolute maximum peak. Features $F_2$ through $F_5$ are selected in a manner previously discussed. Intermediate features may also be computed, but are not shown in FIG. 13A or 14A. For example, a total of eight features may be used for performing FCC computations.

When performing FCC computations, the amplitudes associated with locations of the selected features are stored. For example, and with reference to FIG. 14A in particular, the stored locations associated with the five features, $F_1$-$F_5$, are given as locations [3, 25, 29, 36, 65]. The amplitudes associated with these locations are given as amplitudes [0, 5, 50, −50, 0]. These amplitudes for the features of the currently stored shock channel template and those of the newly detected template beats are used for performing FCC computations associated with an automatic shock channel template update procedure.

Figure 15:
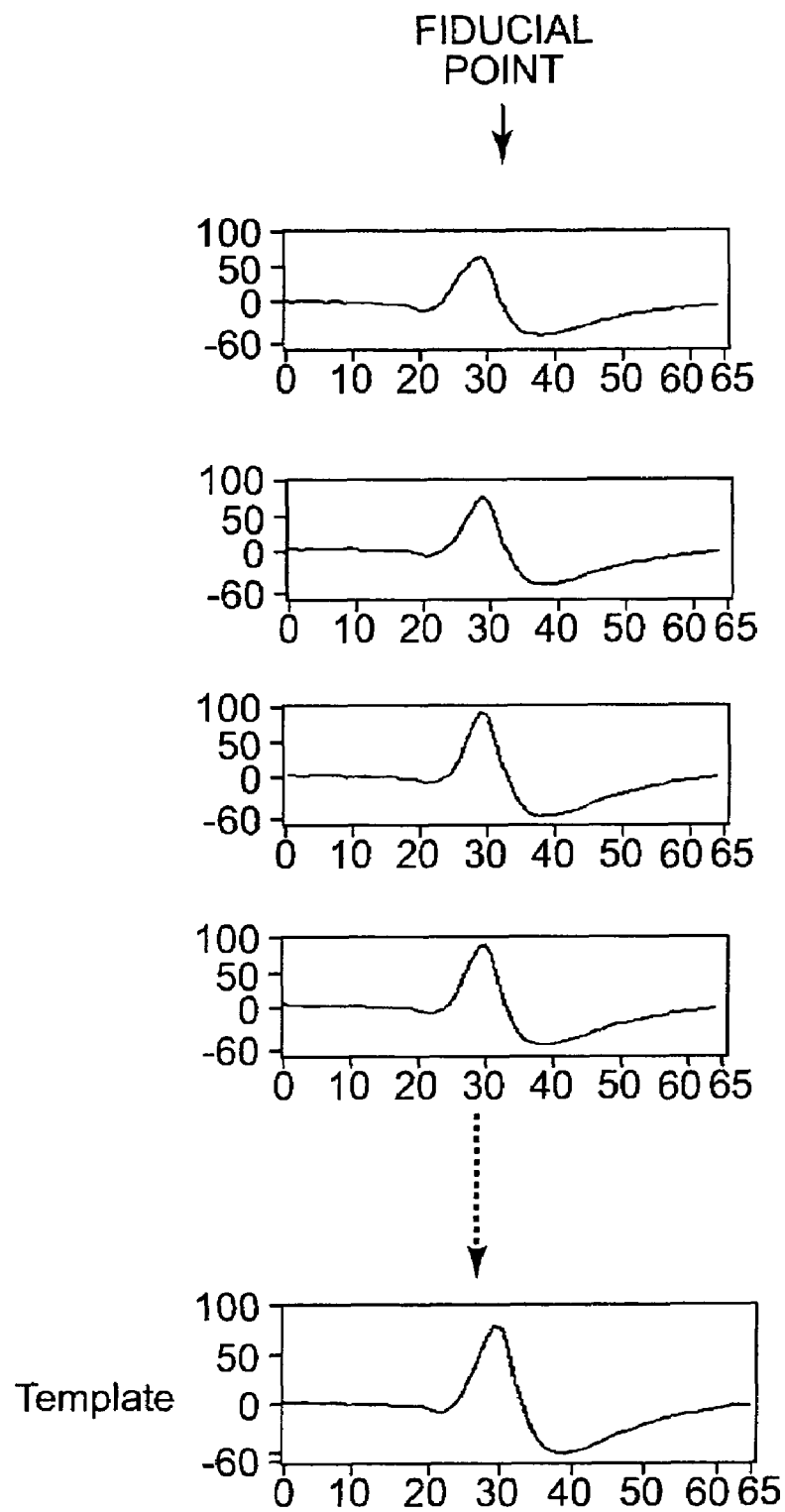
FIG. 15 illustrates generation of a shock channel template by use of a number of averaged template beats aligned with respect to a rate channel fiducial point established in accordance with an embodiment of the present invention.
Figure 16:
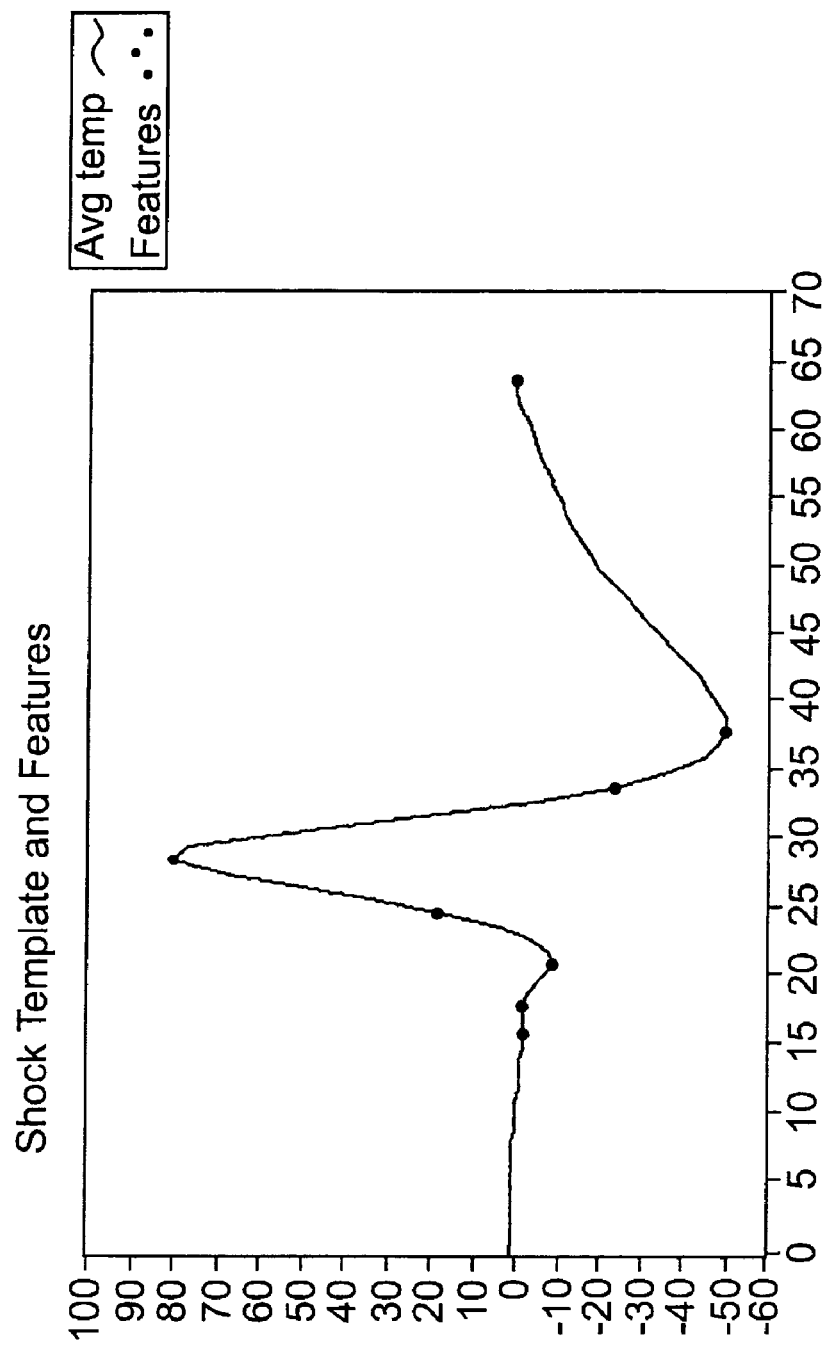
FIG. 16 illustrates the resultant shock channel template of FIG. 16 in greater detail.

As discussed previously, and to summarize by use of the depictions in FIGS. 15 and 16, two channels of continuous egram are employed by the template generation algorithm of the present invention. More particularly, a rate channel and a shock or morphology channel are employed. The template generation algorithm preferably activates on a periodic basis, such as every two hours. It is noted that the wake-up duration is programmable and may be variable. The template generation algorithm performs the following operations.

If a previous template exists and continues to qualify as a snapshot representative of one beat of a patient's normal cardiac rhythm, then the previous template is retained as the current template. Otherwise, an attempt is made to generate a new template. FIGS. 15 and 16 illustrate various stages of template generation in accordance with an embodiment of the present invention.

FIG. 15 depicts a template waveform generated using a detection window consisting of 65 samples centered at the fiducial point (i.e., point 32). FIG. 16 illustrates a shock channel template generated by the aforementioned averaging process, with a number of features selected for the template also being shown. The features are selected in a manner described herein.

Template generation in accordance with the principles of the present invention provides for several advantages. For example, the template generation methodology of the present invention requires only beat-by-beat analysis and is well-suited for use in implantable devices, such as in implantable cardioverter/defibrillator devices. Moreover, the multi-stage approach of the present invention is efficient in its memory usage. Further, the template generation approach of the present invention is robust in generating a snapshot representative of one beat of a patient's normal cardiac rhythm in the presence of premature ventricular complexes (PVCs). The template generation approach of the present invention is well-suited for use in conjunction with a VT/SVT rhythm discrimination system.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of characterizing a patient's cardiac rhythm in an implantable device, comprising:
   sensing cardiac beat signals;
   temporally aligning the cardiac beat signals;
   generating a candidate template using the aligned cardiac beat signals, the candidate template being representative of a cardiac rhythm of a patient;
   storing the candidate template as a current template if a current cardiac rhythm correlates to the candidate template;
   retaining a previously stored template as the current template if the current cardiac rhythm fails to correlate to the candidate template and continuing to use the previously stored template as the current template; and
   using the current template to discriminate a tachyarrhythmia between ventricular tachyarrhythmia and supraventricular tachyarrhythmia.

2. The method of claim 1, wherein temporally aligning the cardiac beat signals comprises:
   extracting feature timing information from the cardiac beat signals; and
   aligning the cardiac beat signals using the extracted feature timing information.

3. The method of claim 1, wherein temporally aligning the cardiac beat signals comprises:
   extracting peak timing information from the cardiac beat signals; and
   aligning the cardiac beat signals using the peak timing information.

4. The method of claim 1, wherein sensing the cardiac beat signals comprises sensing rate channel signals and shock channel signals.

5. The method of claim 1, wherein the cardiac rhythm comprises normal sinus rhythm.

6. The method of claim 1, wherein the cardiac rhythm comprises supra-ventricular rhythm.

7. The method of claim 1, further comprising switching modes of a cardiac defibrillator, wherein generating the cardiac template comprises generating the candidate template responsive to mode switching.

8. The method of claim 1, further comprising detecting connectivity between a cardiac defibrillator and cardiac leads, wherein generating the candidate template comprises generating the candidate template responsive to detecting connectivity between the cardiac defibrillator and cardiac leads.

9. The method of claim 1, further comprising receiving at least one signal from an external programmer, wherein generating the candidate template comprises generating the candidate template responsive to a signal from the external programmer.

10. The method of claim 1, further comprising receiving an input from a clinical user, wherein generating the candidate template comprises generating the candidate template responsive to the input from the clinical user.

11. The method of claim 1, wherein generating the candidate template comprises generating the candidate template according to a programmable template update time period.

12. A system for generating a template of one beat of a patient's cardiac rhythm, comprising:
   a plurality of electrodes configured to be electrically coupled to a heart;
   a sensor system, coupled to the electrodes, the sensor system configured to sense cardiac signal via the electrodes; and
   a processor coupled to the sensor system, the processor configured to temporally align cardiac beat signals, generate a candidate template representative of a cardiac rhythm of a patient using the aligned cardiac beat signals, store the candidate template as a current template if a current cardiac rhythm correlates with the candidate template, retain a previously stored template as the current template if the current cardiac rhythm fails to correlate with the candidate template, use the current template to discriminate a tachyarrhythmia between ventricular tachyarrhythmia and supraventricular tachyarrhythmia.

13. A system of claim 12, wherein the processor is configured to extract feature information from the cardiac signals and align the cardiac beat signals using the extracted feature information.

14. The system of claim 12, wherein the processor is configured to extract peak timing information from the cardiac signals and align the cardiac beat signals using the extracted peak timing information.

15. The system of claim 12, wherein:
   the sensor system is configured to sense rate channel signals and shock channel signals; and
   the processor is configured to extract feature information from the rate channel signals and align the shock channel signals using the feature information extracted from the rate channel signals.

16. The system of claim 12, wherein the processor is configured to switch modes of a cardiac defibrillator and generate the candidate template in response to the mode switching.

17. The system of claim 12, wherein the processor is configured to detect connectivity between the electrodes and the sensor system and generate the candidate template in response to the detection of connectivity between the electrodes and the sensor system.

18. The system of claim 12, further comprising an external controller, communicatively coupled to the processor wherein the processor is configured to receive at least one signal from the external controller and generate the candidate template in response to a signal received from the external controller.

19. The system of claim 12, wherein the processor is configured to receive an input from a clinical user and generate the candidate template in response to the input from the clinical user.

20. The system of claim 12, wherein the control system is configured to detect an event and terminate generation of the candidate template responsive to the detected event.

21. The system of claim 12, wherein the cardiac rhythm comprises normal sinus rhythm.

22. The system of claim 12, wherein the cardiac rhythm comprises supra-ventricular rhythm.

* * * * *